United States Patent
Ma et al.

(10) Patent No.: US 10,538,835 B2
(45) Date of Patent: Jan. 21, 2020

(54) VARIABLY FLEXIBLE METAL ARTICLE AND METHODS OF MAKING THE SAME

(71) Applicant: Adallo LLC, Atlanta, GA (US)

(72) Inventors: Ji Ma, Bryan, TX (US); Ibrahim Karaman, College Station, TX (US); Eric Flickinger, Atlanta, GA (US)

(73) Assignee: Adallo LLC, Atlanta, GA (US)

( * ) Notice: Subject to any disclaimer, the term of this patent is extended or adjusted under 35 U.S.C. 154(b) by 0 days.

(21) Appl. No.: 16/000,470

(22) Filed: Jun. 5, 2018

(65) Prior Publication Data

US 2018/0347023 A1    Dec. 6, 2018

Related U.S. Application Data

(60) Provisional application No. 62/515,390, filed on Jun. 5, 2017, provisional application No. 62/562,144, filed on Sep. 22, 2017.

(51) Int. Cl.
*C22C 14/00* (2006.01)
*C22F 1/18* (2006.01)
*A61L 31/02* (2006.01)

(52) U.S. Cl.
CPC .............. *C22F 1/183* (2013.01); *C22C 14/00* (2013.01); *A61L 31/022* (2013.01)

(58) Field of Classification Search
CPC .................................. C22F 1/183; C22C 14/00
USPC .................. 148/574, 669, 670, 714
See application file for complete search history.

(56) References Cited

U.S. PATENT DOCUMENTS

| | | | |
|---|---|---|---|
| 9,752,219 B2 | 9/2017 | Ma et al. | |
| 2004/0059410 A1 | 3/2004 | Cox | |
| 2005/0049690 A1 | 3/2005 | Boismier | |
| 2010/0016952 A1 | 1/2010 | Prokoshkin | |
| 2014/0076883 A1 | 3/2014 | Brailovski et al. | |
| 2014/0338795 A1* | 11/2014 | Gloriant | C23C 8/24 148/217 |
| 2017/0247774 A1 | 8/2017 | Sachdev et al. | |

OTHER PUBLICATIONS

Carson et al. "Heat Treating of Titanium and Titanium Alloys" ASM Handbook, vol. 4E, Heat Treating of Nonferrous Alloys. pp. 511-534. 2016. (Year: 2016).*
International Search Report and Written Opinion related PCT Application PCT/US2018/036032 dated Jul. 27, 2018, 16 pages.
Liu, Huihong, et al., β—Type Titanium Alloys for Spinal Fixation Surgery with High Young's Modulus Variability and Good Mechanical Properties, ACTA Biomaterialia, Elsevier, www.elsevier.com/locate/actabiomat, vol. 24, Jun. 20, 2015, 9 pages.

* cited by examiner

*Primary Examiner* — Brian D Walck
(74) *Attorney, Agent, or Firm* — Kilpatrick Townsend & Stockton LLP

(57) ABSTRACT

Provided herein are variably flexible (i.e., variably stiff) metal alloys and methods of making the variably flexible (i.e., variably stiff) metal alloys. A variably flexible (i.e., variably stiff) metal alloy is a metal alloy that has areas of differing flexibility (i.e., stiffness, rigidity or elasticity) along a length of the metal alloy when the metal alloy is subjected to a load in use. Also provided herein are methods of making variably flexible (i.e., variably stiff) metal alloys and products including casting a metal alloy and selectively heat treating portions of the metal alloy to achieve predetermined stiffnesses in those portions.

22 Claims, 5 Drawing Sheets

VARIABLY FLEXIBLE METAL ARTICLE AND METHODS OF MAKING THE SAME

CROSS-REFERENCE TO RELATED APPLICATIONS

This application claims the benefit of U.S. Provisional Application Nos. 62/515,390, filed Jun. 5, 2017 and titled "SELF-ADAPTIVE GROWING ROD FOR THE TREATMENT OF PEDIATRIC SCOLIOSIS," and 62/562,144, filed Sep. 22, 2017 and titled "VARIABLY FLEXIBLE METAL ARTICLE AND METHODS OF MAKING THE SAME," the contents of both of which are incorporated herein by reference in their entireties.

TECHNICAL FIELD

The present disclosure relates to metallurgy generally and more specifically to titanium alloys and associated methods.

BACKGROUND

Unless otherwise indicated herein, the materials described in this section are not prior art to the claims in this application and are not admitted to be prior art by inclusion in this section.

Material strength can be directly related to an elastic modulus (e.g., stiffness) of the material. Thus, high-strength engineering materials used in load-bearing applications can be highly rigid. In some engineering applications, high strength can be required and high rigidity can be undesirable. Methods to impart flexibility in a material can be detrimental to the strength. Moreover, material discontinuities can create weak points in the material.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Provided herein are variably elastic metal alloy products (such as variably flexible metal alloy products) and methods of making them. In some cases, the metal alloy product has a location-dependent flexibility (or, likewise, stiffness) that can be achieved in a single titanium alloy.

Described herein are exemplary methods of making a variably flexible metal alloy product that includes casting a metal alloy to provide a metal alloy having an intermediate elastic modulus, heat treating at least a first portion of the metal alloy to train the at least first portion, and thermally insulating any portion not subjected to heat treating to maintain the intermediate elastic modulus of the portion not subjected to heat treating. Casting the metal alloy can include vacuum arc melting, vacuum induction melting, or skull melting. In some cases, the as-cast metal alloy can have at least about 70% beta-phase crystalline structure.

The method can further include quenching the cast metal alloy at a rate sufficient to maintain the at least about 70% beta-phase crystalline structure. The method can further optionally include cold working the metal alloy after casting. Cold working the metal alloy can include cold rolling, wire drawing, extruding, or swaging to at least a 25% reduction in thickness of the metal alloy (e.g., cold rolling) or to at least a 25% reduction in cross-sectional area of the metal alloy (e.g., wire drawing, extruding or swaging).

Heat treating the at least first portion of the metal alloy can train the at least first portion such that, when subjected to loading (e.g., in-service loading when the alloy is in use, test loading, or any suitable applied stress), the at least first portion undergoes a stress induced phase transformation from a beta-phase ($\beta$-phase) to an alpha"-phase ($\alpha$"-phase) crystalline structure, the phase change resulting in a decreased elastic modulus in the at least first portion of the metal alloy under loading. In some non-limiting examples, heat treating the at least first portion of the metal alloy can be performed at a temperature from approximately 150° C. to approximately 1200° C. for approximately 1 minute to approximately 20 minutes.

Thermally insulating any portion not subjected to heat treating to maintain the elastic modulus of the portion not subjected to heat treating can include, for example, direct contact chilling, air cooling, or gas flow cooling.

In some non-limiting examples, the method can further include heat treating at least a second portion of the metal alloy to increase the elastic modulus of the at least second portion. In some cases, heat treating the at least second portion can induce a phase change from the beta-phase ($\beta$-phase) to an alpha-phase ($\alpha$-phase) crystalline structure in the at least second portion. In some non-limiting examples, heat treating the at least second portion of the metal alloy to induce a phase change to an alpha-phase crystalline structure can be performed at a temperature from approximately 400° C. to approximately 650° C. for approximately 6 hours to approximately 168 hours.

In some further cases, heat treating the at least second portion can induce a phase change from the beta-phase ($\beta$-phase) to an omega-phase ($\omega$-phase) crystalline structure in the at least second portion to increase the elastic modulus of the at least second portion. In some non-limiting examples, heat treating the at least second portion of the metal alloy to induce a phase change from the beta-phase to the $\omega$-phase crystalline structure can be performed from approximately 150° C. to approximately 400° C. for approximately 30 minutes to approximately 168 hours.

The heat treating of the first and/or second portions can include at least one of induction heating, laser heating, resistive heating, and/or furnace heating.

Also described herein is a method of tuning heat treating the metal alloy. The tuning heat treating can be performed to fine tune an elastic modulus of a portion of the metal alloy. In some examples, the tuning heat treating creates an omega-phase ($\omega$-phase) crystalline structure in the portion subjected to tuning heat treating. In one non-limiting example, the tuning heat treating is performed at a temperature of from approximately 150° C. to approximately 400° C. for approximately 30 minutes to approximately 168 hours.

Also provided herein are variably flexible (i.e., variably stiff) metal alloy articles, including articles made according to the disclosed methods. In other words, a metal alloy article described herein can have an elastic modulus that varies throughout the article. In one non-limiting example, the alloy comprises approximately 72 atomic percent (at. %) to approximately 78 at. % titanium (Ti), approximately 22 at. % to approximately 28 at. % niobium (Nb), and up to approximately 1 at. % of impurities. In another example, the alloy comprises approximately 70 at. % to approximately 78 at. % titanium (Ti), approximately 18 at. % to approximately 24 at. % niobium (Nb), up to approximately 12 at. % of any one of or any combination of zirconium (Zr), tin (Sn), tantalum (Ta), molybdenum (Mo), iron (Fe), and chromium (Cr), and up to approximately 1 at. % of impurities.

The disclosed variably flexible (i.e., variably stiff) metal alloy articles include at least one rigid portion and at least one flexible portion when subjected to loading (e.g., when subjected to a stress in use). In some cases, the variably flexible (i.e., variably stiff) metal alloy article includes a plurality of rigid portions and a plurality of flexible portions. The variably flexible (i.e., variably stiff) metal alloy article can have an elastic modulus that can vary between approximately 20 GPa to approximately 110 GPa across the metal alloy article. More specifically, in some non-limiting examples, the rigid portion or portions of the article can have an elastic modulus of from approximately 80 GPa to approximately 110 GPa, and the flexible portion or portions of the article can have an elastic modulus of from approximately 20 GPa to approximately 40 GPa. The plurality of rigid portions and the plurality of flexible portions can be controllably distributed across the variably flexible (i.e., variably stiff) metal alloy article.

The variably flexible (i.e., variably stiff) metal alloy article can be used in any suitable application. Some non-limiting examples include a medical device, a medical implant, sporting goods, a transportation structural part, an automotive structural part, an automotive aesthetic part, an aerospace structural part, or an aerospace aesthetic part. Some further non-limiting examples include spinal rods for degeneration and deformity corrections, fracture stabilization devices such as plates or intramedullary nails, stems for hip, knee, shoulder and hand/foot joint replacements, spinal interbody cages, endoprostheses, dental implants, fishing rods, tennis racquets, and golf clubs.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
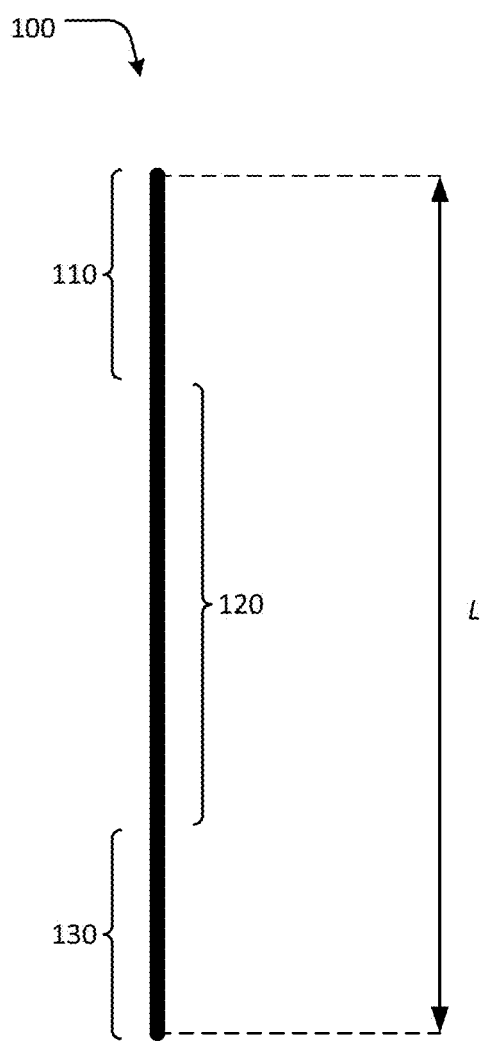
FIG. 1 is a schematic illustration of an exemplary alloy rod according to certain aspects of the present disclosure.

Certain aspects and features of the present disclosure relate to a variably flexible (i.e., variably stiff) metal alloy article and methods of making the variably flexible (i.e., variably stiff) metal alloy article. In some cases, the variably flexible (i.e., variably stiff) metal alloy is a variably flexible (i.e., variably stiff) titanium alloy. A variably flexible (i.e., variably stiff) metal alloy is a metal alloy that is trained to have areas of differing flexibility (i.e., stiffness, rigidity or elasticity) along a length of the metal alloy when the metal alloy is subjected to loading (i.e., the metal alloy is stressed as a result of being placed in a dynamic system, for example a spinal implant implanted in the body or a shaft of a golf club during a swing). In some examples, a variably flexible metal alloy article can be a variably flexible metal round bar (e.g., a rod), a variably flexible metal flat bar, a variably flexible metal rectangular bar, a variably flexible metal square bar, a variably flexible metal hexagonal bar, a variably flexible metal channel, a variably flexible metal beam, a variably flexible metal angle, a variably flexible metal tread plate, a variably flexible metal expanded sheet, a variably flexible metal perforated sheet, a variably flexible metal mesh sheet, a variably flexible metal pipe, a variably flexible metal round tube, a variably flexible metal square tube, a variably flexible metal rectangular tube, a variably flexible metal hollow bar, a variably flexible metal shafting, a variably flexible metal drill rod, a variably flexible metal precision ground stock, a variably flexible metal plate, a variably flexible metal sheet, any combination thereof, or any suitable metal article. In some non-limiting examples, the variably flexible (i.e., variably stiff) metal alloy article (such as a rod) of length L can have a flexible area of length f and a rigid area of length R such that f+R=L. In some further non-limiting examples, the variably flexible (i.e., variably stiff) metal alloy rod of length L can have a plurality of flexible areas of length f and a rigid area of length R such that ((number of flexible areas)×f)+R=L. In still further non-limiting examples, the variably flexible (i.e., variably stiff) metal alloy rod of length L can have a plurality of flexible areas of length f and a plurality of rigid areas of length R such that ((number of flexible areas)×f)+((number of rigid areas)×R)=L. In still further non-limiting examples, the variably flexible (i.e., variably stiff) metal alloy of length L can have a flexible area of length f and a plurality of rigid areas of length R such that f+((number of rigid areas)×R)=L. Thus, when placed under a load, any rigid areas can hold a shape and any flexible areas can yield under a force applied by the load and flex as desired. For example, in a golf club during a swing, a golfer can desire a portion of the golf club serving as a handle to remain rigid and concomitantly desire a portion of the golf club adjacent to a club head to articulate to increase striking force to a golf ball. As another example, in a spinal rod implanted in a patient, the spinal rod can have more flexibility towards its ends to reduce the stress on bone and screw anchors, but greater rigidity in its center to maintain curve correction for treating scoliosis or other conditions.

In some aspects, each flexible area in the plurality of flexible areas can have any length less than or equal to the length L (i.e., a total length of the metal alloy rod, see FIG. 1) such that the plurality of flexible areas can include a plurality of lengths f of the flexible areas. In some further aspects, each rigid area in the plurality of rigid areas can have any length less than or equal to the length L (i.e., a total length of the metal alloy rod) such that the plurality of rigid areas can include a plurality of lengths R of the rigid areas. If the metal alloy rod includes a plurality of flexible areas and a plurality of rigid areas, each of the flexible areas may be trained to have the same or different flexibilities (i.e., elastic moduli) and each of the rigid areas may have the same or different flexibilities.

In some non-limiting examples, one or more areas can be heat treated to have a distinct stiffness from the other areas.

Thus, in some aspects, a single alloy article having a length L can have a predetermined plurality of stiffnesses across its length. For example, a metal alloy having a length L can have a first area (i.e., a first portion) having a first stiffness A and length M, a second area (i.e., a second portion) having a second stiffness B and length N, and a third area having a third stiffness C and length O, such that M+N+O=L. In some cases, A≠B≠C. In some other cases, A=C≠B, or any combination thereof.

In the example of FIG. 1, the first portion 110 of the variably flexible (i.e., variably stiff) metal alloy rod 100 can have a first stiffness (e.g., first elastic modulus), the second portion 120 can have a second stiffness (e.g., a second elastic modulus), and the third portion 130 can have a third stiffness (e.g., a third elastic modulus). In some cases, the first stiffness of the first portion 110 is the same as the third stiffness of the third portion 130, although it need not be.

In some non-limiting examples, an as-cast metal alloy article (e.g., a titanium-niobium (TiNb) alloy rod) can have a single stiffness across all portions of the as-cast metal alloy article (i.e., an entire single metal alloy article as cast has a single elastic modulus). In some non-limiting examples, the single stiffness of the as-cast metal alloy article can be referred to as an intermediate elastic modulus. In some non-limiting examples, a majority of the as-cast metal alloy article can be a beta-phase (β-phase) metal alloy. In some examples, at least approximately 70% of the as-cast (and in some cases cold worked) metal alloy article can be a β-phase metal alloy. For example, at least approximately 70% of the as-cast metal alloy article can be a β-phase metal alloy, at least approximately 71% of the as-cast metal alloy article can be a β-phase metal alloy, at least approximately 72% of the as-cast metal alloy article can be a β-phase metal alloy, at least approximately 73% of the as-cast metal alloy article can be a β-phase metal alloy, at least approximately 74% of the as-cast metal alloy article can be a β-phase metal alloy, at least approximately 75% of the as-cast metal alloy article can be a β-phase metal alloy, at least approximately 76% of the as-cast metal alloy article can be a β-phase metal alloy, at least approximately 77% of the as-cast metal alloy article can be a β-phase metal alloy, at least approximately 78% of the as-cast metal alloy article can be a β-phase metal alloy, at least approximately 79% of the as-cast metal alloy article can be a β-phase metal alloy, at least approximately 80% of the as-cast metal alloy article can be a β-phase metal alloy, at least approximately 81% of the as-cast metal alloy article can be a β-phase metal alloy, at least approximately 82% of the as-cast metal alloy article can be a β-phase metal alloy, at least approximately 83% of the as-cast metal alloy article can be a β-phase metal alloy, at least approximately 84% of the as-cast metal alloy article can be a β-phase metal alloy, at least approximately 85% of the as-cast metal alloy article can be a β-phase metal alloy, at least approximately 86% of the as-cast metal alloy article can be a β-phase metal alloy, at least approximately 87% of the as-cast metal alloy article can be a β-phase metal alloy, at least approximately 88% of the as-cast metal alloy article can be a β-phase metal alloy, at least approximately 89% of the as-cast metal alloy article can be a β-phase metal alloy, at least approximately 90% of the as-cast metal alloy article can be a β-phase metal alloy, at least approximately 91% of the as-cast metal alloy article can be a β-phase metal alloy, at least approximately 92% of the as-cast metal alloy article can be a β-phase metal alloy, at least approximately 93% of the as-cast metal alloy article can be a β-phase metal alloy, at least approximately 94% of the as-cast metal alloy article can be a β-phase metal alloy, at least approximately 95% of the as-cast metal alloy article can be a β-phase metal alloy, at least approximately 96% of the as-cast metal alloy article can be a β-phase metal alloy, at least approximately 97% of the as-cast metal alloy article can be a β-phase metal alloy, at least approximately 98% of the as-cast metal alloy article can be a β-phase metal alloy, or at least approximately 99% of the as-cast metal alloy article can be a β-phase metal alloy.

The metal alloy article can then be heat treated to obtain a variably flexible (i.e., variably stiff) metal alloy article when the article is subjected to loading (i.e., the metal alloy can be trained to have variable flexibility when subjected to loading when in use). For example, heat treating a portion of the metal alloy article can train the portion of the metal alloy article such that it undergoes a stress induced phase transformation from the β-phase to the α"-phase crystalline structure when subjected to loading, thus providing a decreased elastic modulus in that portion when the metal alloy article is subjected to loading (such as when in use). Thus, subjecting the metal alloy article to loading after training at least one portion of the article can reduce an elastic modulus of that at least one portion of the metal alloy article, providing a more flexible portion of the metal alloy article. Heat treating a portion of the metal alloy article such that the elastic modulus of that portion of the metal alloy article is decreased when subjected to loading can be referred to as a softening heat treatment. In some cases, the elastic modulus of the portion subjected to the softening heat treatment is not reduced until the article is subjected to loading (such as in use, when stress is applied to the article). Manipulating a portion of the alloy in a way that decreases the modulus of elasticity of that portion when subjected to loading (e.g., applying the softening heat treatment) is sometimes referred to herein as training that portion of the article.

In some examples, during the softening heat treatment, any portion of the metal alloy article not subjected to the softening heat treatment can be thermally insulated or otherwise cooled to confine the softening heat treatment to the portion of the metal alloy article subjected to the softening heat treatment while maintaining the rest of the metal article at the intermediate elastic modulus as-cast.

In some examples, the softening heat treatment can train select portions of the article such that, upon subsequent loading (e.g., in-service loading when the article is in use), the trained portions undergo a phase change from the β-phase to the α"-phase. The phase change from the β-phase to the α"-phase can be a martensitic phase change, providing a reduced elastic modulus (i.e., a more flexible metal alloy) in the trained portions. In some aspects, when the loading is removed (e.g., the in-use load is no longer applied), the trained portion of the metal alloy article can undergo a reversing phase change from the α"-phase to the β-phase and return to the intermediate elastic modulus.

In some non-limiting examples, one or more portions of the variably flexible (i.e., variably stiff) metal alloy article not subjected to the softening heat treatment (e.g., one or more second portions of the variably elastic metal alloy article) can be subjected to an optional heat treatment to increase an elastic modulus of the one or more second portion. In some examples, optionally heat treating the one or more second portions of the variably flexible (i.e., variably stiff) metal alloy article to increase the elastic modulus of the one or more second portions can be referred to as a stiffening heat treatment. In some further examples, during the optional stiffening heat treatment, any portion of the metal alloy article not subjected to the stiffening heat treatment can be thermally insulated or otherwise cooled to confine the stiffening heat treatment to the portion of the metal alloy article subjected to the stiffening heat treatment.

In some examples, the stiffening heat treatment can cause a phase change in the metal alloy article from the β-phase to an alpha-phase (α-phase). The phase change from the β-phase to the α-phase can provide an increased elastic modulus (i.e., a more rigid metal alloy). In some cases, the stiffening heat treatment can cause a phase change from the β-phase to an omega-phase (ω-phase) to provide an increased elastic modulus.

In some further cases, after the softening heat treatment, the stiffening heat treatment can be applied to the portion of the metal alloy article subjected to the softening heat treatment to fine tune the elastic modulus of that portion by creating an inconsistent ω-phase (i.e., only sporadic portions of the crystal structure are changed to the ω-phase). The inconsistent ω-phase can locally prevent the phase change from the β-phase to the α"-phase when the article is subjected to loading, thus providing an increased elastic modulus in the trained portion of the metal alloy to slightly strengthen the trained portion of the metal alloy article (i.e., the portion of the metal alloy article subjected to the softening heat treatment).

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

The terms "invention," "the invention," "this invention" and "the present invention" used herein are intended to refer broadly to all of the subject matter of this patent application and the claims below. Statements containing these terms should be understood not to limit the subject matter described herein or to limit the meaning or scope of the patent claims below.

The following titanium alloys are described in terms of their elemental composition in atomic percentage (at. %) based on the total atomic weight of the alloy. In certain examples of each alloy, the remainder is titanium, with a maximum of 1 at. % for the sum of the impurities.

As used herein, the meaning of "a," "an," or "the" includes singular and plural references unless the context clearly dictates otherwise.

All ranges disclosed herein encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more, e.g. 1 to 6.1, and ending with a maximum value of 10 or less, e.g., 5.5 to 10.

As used herein, the meaning of "room temperature" can include a temperature of from about 15° C. to about 30° C., for example about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., or about 30° C.

Alloy Composition

In some non-limiting examples, a metal alloy including titanium (Ti) and niobium (Nb) as predominant alloying elements can provide a titanium-niobium (TiNb) based alloy having controllable elastic properties. The elastic properties of the metal alloy can be controlled through exemplary processing to provide an article whose elastic modulus varies throughout the article when subjected to loading. In some examples, after processing to soften and/or stiffen select portions of the metal alloy, the elastic modulus varies throughout the metal alloy between about 20 GPa and about 110 GPa when subjected to loading.

In some non-limiting examples, a TiNb based alloy with controllable elastic properties can have the following elemental compositions as provided in Table 1 (all values in atomic %):

TABLE 1

| Alloy Compositions | |
|---|---|
| Element | Atomic Percent (at. %) |
| Ti | 72%-78% |
| Nb | 22%-28% |
| Impurities | Up to 1% |

In some non-limiting examples, a TiNbX (wherein X is selected from the group consisting of zirconium (Zr), tin (Sn), chromium (Cr), molybdenum (Mo), iron (Fe), and tantalum (Ta)) based alloy can have the following elemental compositions as provided in Table 2 (all values in atomic %):

TABLE 2

| Alloy Compositions | |
|---|---|
| Element | Atomic Percent (at. %) |
| Ti | 70%-78% |
| Nb | 18%-24% |
| X (Zr, Sn, Cr, Mo, Fe, and/or Ta) | Up to 12% |
| Impurities | Up to 1% |

In certain aspects, the alloy includes titanium (Ti) in an amount of from about 70% to about 78% (e.g., from about 71% to about 77%, from about 72% to about 78%, from about 76% to about 77%, or from about 70% to about 75%) based on the total atomic weight of the alloy. For example, the alloy can include about 70.0%, about 70.1%, about 70.2%, about 70.3%, about 70.4%, about 70.5%, about 70.6%, about 70.7%, about 70.8%, about 70.9%, about 71.0%, about 71.1%, about 71.2%, about 71.3%, about 71.4%, about 71.5%, about 71.6%, about 71.7%, about 71.8%, about 71.9%, about 72.0%, about 72.1%, about 72.2%, about 72.3%, about 72.4%, about 72.5%, about 72.6%, about 72.7%, about 72.8%, about 72.9%, about 73.0%, about 73.1%, about 73.2%, about 73.3%, about 73.4%, about 73.5%, about 73.6%, about 73.7%, about 73.8%, about 73.9%, about 74.0%, about 74.1%, about 74.2%, about 74.3%, about 74.4%, about 74.5%, about 74.6%, about 74.7%, about 74.8%, about 74.9%, about 75.0%, about 75.1%, about 75.2%, about 75.3%, about 75.4%, about 75.5%, about 75.6%, about 75.7%, about 75.8%, about 75.9%, about 76.0%, about 76.1%, about 76.2%, about 76.3%, about 76.4%, about 76.5%, about 76.6%, about 76.7%, about 76.8%, about 76.9%, about 77.0%, about 77.1%, about 77.2%, about 77.3%, about 77.4%, about 77.5%, about 77.6%, about 77.7%, about 77.8%, about 77.9%, or about 78.0% Ti. All expressed in at. %.

In certain aspects, the alloy also includes niobium (Nb) in an amount from about 18.0% to about 28.0% (e.g., from about 18.0% to about 24.0%, from about 22.0% to about 28.0%) based on the total atomic weight of the alloy. For example, the alloy can include about 18.0%, about 18.1%, about 18.2%, about 18.3%, about 18.4%, about 18.5%, about 18.6%, about 18.7%, about 18.8%, about 18.9%, about 19.0%, about 19.1%, about 19.2%, about 19.3%, about 19.4%, about 19.5%, about 19.6%, about 19.7%, about 19.8%, about 19.9%, about 20.0%, about 20.1%, about 20.2%, about 20.3%, about 20.4%, about 20.5%, about 20.6%, about 20.7%, about 20.8%, about 20.9%, about 21.0%, about 21.1%, about 21.2%, about 21.3%, about 21.4%, about 21.5%, about 21.6%, about 21.7%, about 21.8%, about 21.9%, about 22.0%, about 22.1%, about 22.2%, about 22.3%, about 22.4%, about 22.5%, about 22.6%, about 22.7%, about 22.8%, about 22.9%, about 23.0%, about 23.1%, about 23.2%, about 23.3%, about 23.4%, about 23.5%, about 23.6%, about 23.7%, about 23.8%, about 23.9%, about 24.0%, about 24.1%, about 24.2%, about 24.3%, about 24.4%, about 24.5%, about 24.6%, about 24.7%, about 24.8%, about 24.9%, about 25.0%, about 25.1%, about 25.2%, about 25.3%, about 25.4%, about 25.5%, about 25.6%, about 25.7%, about 25.8%, about 25.9%, about 26.0%, about 26.1%, about 26.2%, about 26.3%, about 26.4%, about 26.5%, about 26.6%, about 26.7%, about 26.8%, about 26.9%, about 27.0%, about 27.1%, about 27.2%, about 27.3%, about 27.4%, about 27.5%, about 27.6%, about 27.7%, about 27.8%, about 27.9%, or about 28.0% Nb. All expressed in at. %.

In certain aspects, the alloy includes one or more of zirconium (Zr), tin (Sn), chromium (Cr), molybdenum (Mo), iron (Fe), or tantalum (Ta) in an amount (in total) up to about 12.0% (e.g., from about 0% to about 2%, from 0.01% to 8.2%, from 2.0% to 8.0%, from 5.0% to 10.0%, or from 6.2% to 9.9%) based on the total atomic weight of the alloy. For example, the alloy can include about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0%, about 10.1%, about 10.2%, about 10.3%, about 10.4%, about 10.5%, about 10.6%, about 10.7%, about 10.8%, about 10.9%, about 11.0%, about 11.1%, about 11.2%, about 11.3%, about 11.4%, about 11.5%, about 11.6%, about 11.7%, about 11.8%, about 11.9%, or about 12.0% of one or more of Zr, Sn, Cr, Mo, Fe, and/or Ta in total. In certain aspects, one or more of Zr, Sn, Cr, Mo, Fe, and Ta are not present in the alloy (i.e., 0.0%). All expressed in at. %.

Optionally, the alloy can further include other minor elements, sometimes referred to as impurities, in amounts of about 1% or below, about 0.9% or below, about 0.8% or below, about 0.7% or below, or about 0.6% or below, about 0.5% or below, about 0.4% or below, about 0.3% or below, about 0.2% or below, or about 0.1% or below, total. These impurities may include, but are not limited to, nitrogen (N), oxygen (O), manganese (Mn), copper (Cu), yttrium (Y), aluminum (Al), nickel (Ni), silver (Ag), boron (B), bismuth (Bi), gallium (Ga), lithium (Li), lead (Pb), vanadium (V), calcium (Ca), hafnium (Hf), strontium (Sr), scandium (Sc) or combinations thereof. Accordingly, N, O, Mn, Cu, Y, Al, Ni, Ag, B, Bi, Ga, Li, Pb, V, Ca, Hf, Sr, or Sc may be present in an alloy in amounts of about 1% or below, about 0.9% or below, about 0.8% or below, about 0.7% or below, or about 0.6% or below, about 0.5% or below, about 0.4% or below, about 0.3% or below, about 0.2% or below, or about 0.1% or below. In certain aspects, the sum of all impurities does not exceed approximately 1% (e.g., 0.75%). All expressed in at. %. In certain aspects, the remaining percentage of the alloy is titanium and niobium. In some cases, the remaining percentage of the alloy is titanium, niobium and zirconium. In some further cases, the remaining percentage of the alloy is titanium, niobium and tin. In some still further cases, the remaining percentage of the alloy is titanium, niobium and tantalum.

In one non-limiting example, an exemplary alloy includes about 74% Ti, about 26% Nb ($Ti_{74}Nb_{26}$), and up to about 1% impurities, referred to as "Alloy A" below. All expressed in at. %.

Another exemplary alloy includes about 75% Ti, about 25% Nb ($Ti_{75}Nb_{25}$), and up to about 1% impurities. All expressed in at. %.

Methods of Making

In some non-limiting examples, the alloys described herein can be subjected to processing methods including casting, homogenizing, softening heat treatments, and thermally insulating to produce a variably flexible (i.e., variably stiff) metal alloy article. Optional processing steps include cold working and stiffening heat treatments as described below. For example, an exemplary Method A can include casting, homogenizing, cold working, softening heat treatment, thermally insulating, and optional stiffening heat treatment. An exemplary Method B can include casting, homogenizing, softening heat treatment, thermally insulating, and optional stiffening heat treatment.

Casting and Homogenizing

In some non-limiting examples, the alloys described herein can be produced through a melting method that can include vacuum arc melting, vacuum induction melting, skull melting or any other suitable melting or casting process to provide a cast alloy. The cast alloy can then be homogenized. In some examples, the alloy can be homogenized at a temperature of from about 900° C. to about 1200° C. For example, the alloy can be homogenized at about 900° C., about 925° C., about 950° C., about 975° C., about 1000° C., about 1025° C., about 1050° C., about 1075° C., about 1100° C., about 1125° C., about 1150° C., about 1175° C., or about 1200° C. In some cases, the alloy can be homogenized for about 1 hour to about 100 hours. For example, the alloy can be homogenized for about 1 hour, about 5 hours, about 10 hours, about 15 hours, about 20 hours, about 25 hours, about 30 hours, about 35 hours, about 40 hours, about 45 hours, about 50 hours, about 55 hours, about 60 hours, about 65 hours, about 70 hours, about 75 hours, about 80 hours, about 85 hours, about 90 hours, about 95 hours, or about 100 hours. In some cases, the cast alloy can be cooled after casting or after casting and homogenizing at a rate of from approximately 0.1° C./second (° C./s) to approximately 1000° C./s (e.g., approximately 0.1° C./s, approximately 1.0° C./s, approximately 10° C./s, approximately 50° C./s, approximately 100° C./s, approximately 500° C./s, approximately 1000° C./s, or anywhere in between).

In some examples, the as-cast alloy has an intermediate elastic modulus (e.g., an intermediate stiffness) of approximately 60-80 GPa (e.g., approximately 60 GPa, approximately 65 GPa, approximately 70 GPa, approximately 75 GPa, approximately 80 GPa, or anywhere in between). The melting method and cooling rate can govern the intermediate elastic modulus. In some examples, the as-cast alloy is a majority beta (β) phase metal alloy, providing the intermediate elastic modulus. In some examples, the metal alloy after casting is about 70% β-phase or more, such as about 80% β-phase or more, about 90% β-phase or more, or anywhere in between. Cooling the as-cast metal alloy can be performed at a rate sufficiently slow to preserve the β-phase as cast. Not to be bound by theory, cooling too slowly can cause a phase change from a β-phase to an α-phase. In some examples, the metal alloy after cooling remains about 70% β-phase, about 80% β-phase, or about 90% β-phase.

Softening Heat Treatment

As mentioned above, at least a first portion of the metal alloy can be subjected to a softening heat treatment to train the at least first portion of the metal alloy such that, when the metal alloy is subjected to a subsequent loading (e.g., in-service loading when in use), a phase change from the β-phase to the α"-phase occurs in the trained at least first portion, thereby decreasing the elastic modulus in the trained at least first portion when the metal alloy is subjected to loading (e.g., when in use). Heat treating the at least first portion can be performed by induction heating, laser heating, resistive heating, furnace heating, or any other suitable heating or any combination thereof. In one exemplary method, at least a first portion of the intermediary alloy described above can be subjected to heat treating to train the at least first portion such that the elastic modulus of the at least first portion is reduced when subjected to loading. Referring to FIG. 1, the metal alloy article 100 can have two first portions 110, 130. The first portions 110, 130 are subjected to the softening heat treatment in a manner sufficient to train the first portions 110, 130. Training the first portions 110, 130 reduces the elastic modulus of the first portions 110, 130 relative to the remainder of the metal alloy 100 when the metal alloy article 100 is subjected to subsequent loading (e.g., when the metal alloy article 100 is in use). The first portions 110, 130 can be heat treated (trained) such that the reduced elastic moduli of each of the first portions 110, 130 are the same after the metal alloy 100 is subjected to loading as described above, or they can be heat treated (trained) so the elastic moduli of the two first portions 110, 130 are different from one another after the metal alloy article 100 is subjected to loading.

The softening heat treatment can be performed up to a limit; up to the limit, increasing the duration of heat treatment will reduce the elastic modulus after subsequent loading of the at least first portion (e.g., first portions 110, 130). In some cases, heat treating the at least first portion of the metal alloy having the intermediate elastic modulus can be performed until a minimum in the first portion's elastic modulus is obtained. In general, as the heat treatment temperature is increased, the heat treatment duration should be shortened accordingly, and vice versa. In some cases, heat treating beyond the limit can plasticize the metal alloy, providing a rigid and/or brittle metal alloy.

In some examples, heat treating the at least first portion in the described manner can train the at least first portion such that the elastic modulus of the at least first portion decreases when the article is subjected to subsequent loading. In some cases, a decreased elastic modulus of the trained at least first portion can be about 40 to about 20 GPa after subsequent loading. For example, the elastic modulus of the at least first portion can be decreased due to the softening heat treatment and subsequent loading from the intermediate elastic modulus to a decreased elastic modulus of about 40 GPa, 30 GPa, 20 GPa, or anywhere in between.

In this way, selective softening heat treatment of one or more portions of the metal alloy having an intermediate elastic modulus as described above can provide a variably flexible (i.e., variably stiff) metal alloy having a plurality of elastic moduli over a length of the variably flexible (i.e., variably stiff) metal alloy. In particular, referring to FIG. 1, the first portions 110, 130 of the variably flexible (i.e., variably stiff) metal alloy article 100 can have a lower elastic modulus than the remainder of the alloy (e.g., the second portion 120) when subjected to subsequent loading.

Thermally Insulating

Thermal conduction can lead to heat treating an undesired portion and imparting an unintentional heat treatment. Thus, in some non-limiting examples, portions of the metal alloy that are not subjected to the softening heat treatment (e.g., the second portion 120 in FIG. 1) can be thermally insulated or chilled while the at least first portion is subjected to softening heat treatment to prevent any proximal heat treating of the second portion 120. Thermally insulating (or chilling) the second portion 120 during softening heat treatment of one or both first portions 110, 130 can prevent thermal conduction from portions intentionally heat treated (e.g., first portions 110, 130) to portions where heat treatment is not desired (e.g., second portion 120).

Some non-limiting examples of such active thermally insulating include, but are not limited to, direct contact chilling, air cooling, gas flow cooling, or any combination thereof. Chilling can help maintain the portions not subjected to softening heat treating (e.g., portions except for first portions 110, 130) at about room temperature (e.g., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., or anywhere in between) to maintain the intermediate elastic modulus and provide selective heat treating of only the at least first portion of the alloy as desired.

Stiffening Heat Treatment

Optionally, at least a second portion of the variably elastic metal alloy is subjected to a stiffening heat treatment to increase the elastic modulus of the at least second portion by inducing a phase change from the β-phase to the α-phase or the ω-phase. In FIG. 1, second portion 120 may be subjected to local stiffening heat treatment sufficient to increase the elastic modulus of the second portion 120 relative to the remainder of the metal alloy article 100 (e.g., first portions 110, 130). In some cases, after the stiffening heat treatment, the at least second portion has a modulus of elasticity between about 90 GPa and about 110 GPa (e.g., about 90 GPa, about 100 GPa, about 110 GPa, or anywhere in between). Heat treating the second portion 120 can be performed by induction heating, laser heating, resistive heating, furnace heating, or any other suitable heating or any combination thereof.

In some cases, the metal alloy is not subjected to the stiffening heat treatment. In such an instance, referring to FIG. 1, the second portion 120 is not heat treated. If the alloy is not subjected to stiffening heat treating, the at least second portion (e.g., second portion 120) can have an elastic modulus that is similar to or the same as the intermediate elastic modulus of the as-cast metal alloy (e.g., having an elastic modulus of about 60 GPa to about 80 GPa), and thus have an elastic modulus that is greater than the elastic modulus of the at least first portion (e.g., first portions 110, 130) after being trained via the softening heat treatment and subsequently loaded.

Method A

Provided herein is a first exemplary method of making a variably elastic metal alloy article, such as an article formed from the alloys disclosed above. The method includes (i) casting a metal alloy, homogenizing the cast metal alloy, and cooling the cast metal alloy as described above, (ii) cold working the cast metal alloy, (iii) heat treating at least a first portion of the metal alloy to train the at least first portion (e.g., the softening heat treatment as described above), and (iv) optionally heat treating at least a second portion of the metal alloy to increase a modulus of elasticity of the at least second portion (e.g., the stiffening heat treatment as described above). In some cases, the method includes thermally insulating portions of the metal alloy not subjected to heat treating while the select portions are heat treated, as described above.

Cold Working

After casting, homogenizing, and cooling as described above, the cast alloy can be subjected to cold working (e.g., cold rolling, wire drawing, extruding, swaging or other suitable cold working). If the cast alloy is cold rolled, in some cases the cold rolling achieves at least about a 25% reduction in thickness of the cast product (e.g., about 25%, about 30%, about 35%, about 40%, about 45%, about 50%, about 55%, about 60%, about 65%, about 70%, about 75%, about 80%, about 85%, about 90%, about 95%, about 99%, or anywhere in between, reduction in thickness). In some cases, wire drawing, extruding, swaging or other suitable cold working includes reducing a cross-sectional area of the cast alloy by at least a 25% reduction (e.g., about 25%, about 30%, about 35%, about 40%, about 45%, about 50%, about 55%, about 60%, about 65%, about 70%, about 75%, about 80%, about 85%, about 90%, about 95%, about 99%, or anywhere in between, reduction in cross-sectional area). Cold working can be performed at temperatures of about room temperature (e.g., about 15° C. to about 30° C.) to about 300° C. For example, cold rolling can be performed at about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 100° C., about 125° C., about 150° C., about 175° C., about 200° C., about 225° C., about 250° C., about 275° C., about 300° C., or anywhere in between. Cold working the cast alloy can provide a high-strength alloy having an intermediate elastic modulus. In some examples, the alloy after cold working can have an intermediate elastic modulus of approximately 60-80 GPa. The high-strength, cold-worked alloy having an intermediate elastic modulus can be an intermediary alloy ready for further processing.

In some examples, cold working the metal alloy to at least a 25% reduction (e.g., in thickness, diameter, cross-sectional area, or any other suitable dimension) can strengthen the metal alloy to prevent plastic deformation and provide a metal alloy having an intermediary elastic modulus that can be tuned during subsequent processing.

Softening Heat Treatment

In some cases, after cold working, portions of the metal alloy can be selectively subjected to softening heat treatment to selectively reduce the elastic modulus of those portions of the metal alloy after subsequent loading. For example, after cold working, at least a first portion of the metal alloy (e.g., first portions 110, 130 in FIG. 1) can be subjected to the softening heat treatment to train the metal alloy such that, when the metal alloy is subjected to subsequent loading (e.g., when the metal alloy is in use), the applied stress can induce a phase change of the at least first portion from the β-phase to the α"-phase, thus decreasing the elastic modulus of the at least first portion. Heat treating the at least first portion can be performed by induction heating, laser heating, resistive heating, furnace heating, or any other suitable heating or any combination thereof. In some examples, the applied stress (e.g., loading) required to induce the phase change from the β-phase to the α"-phase (i.e., a threshold stress) can range from about 20 MPa to about 250 MPa. For example, the threshold stress can be about 20 MPa, 30 MPa, 40 MPa, 50 MPa, 60 MPa, 70 MPa, 80 MPa, 90 MPa, 100 MPa, 110 MPa, 120 MPa, 130 MPa, 140 MPa, 150 MPa, 160 MPa, 170 MPa, 180 MPa, 190 MPa, 200 MPa, 210 MPa, 220 MPa, 230 MPa, 240 MPa, 250 MPa, or anywhere in between.

In some examples, the softening heat treatment can be performed at a temperature of from about 150° C. to about 1200° C. (e.g., about 250° C., about 750° C., about 1100° C., or about 600° C.). For example, the softening heat treatment can be performed at a temperature of about 150° C., 175° C., 200° C., 225° C., 250° C., 275° C., 300° C., 325° C., 350° C., 375° C., 400° C., 425° C., 450° C., 475° C., 500° C., 525° C., 550° C., 575° C., 600° C., 625° C., 650° C., 675° C., 700° C., 725° C., 750° C., 775° C., 800° C., 825° C., 850° C., 875° C., 900° C., 925° C., 950° C., 975° C., 1000° C., 1025° C., 1050° C., 1075° C., 1100° C., 1125° C., 1150° C., 1175° C., 1200° C., or anywhere in between. The softening heat treatment can be performed from about 1 minute to about 20 minutes (e.g., 5 minutes, 10 minutes, or 15 minutes). For example, the softening heat treatment can be performed for about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, or anywhere in between.

In one non-limiting example, applying a softening heat treatment to select portions of a titanium-niobium (TiNb) alloy at about 600° C. for about 15 minutes will train the alloy such that, when the TiNb alloy is subjected to subsequent loading, the alloy will undergo a phase change from the β-phase to the α"-phase in the portions of the TiNb alloy subjected to the softening heat treatment. This phase change decreases the elastic modulus of the select portions trained by the softening heat treatment. In some cases, heating at a lower temperature can require an increase in heating time, and vice versa. In some examples, as described above, portions of the metal alloy not subjected to the softening heat treatment can be thermally insulated to prevent unintentional heat treating of the portions of the metal alloy not being subjected to the softening heat treatment.

In some examples, heat treating the at least first portion to train the alloy and subjecting the alloy to subsequent loading in the described manner can decrease the elastic modulus of the at least first portion from the intermediate elastic modulus of between about 60 GPa to about 80 Ga to a decreased elastic modulus. In some examples after loading of the trained at least first portion the decreased modulus of elasticity can be from about 40 to about 20 GPa. For example, the decreased elastic modulus can be about 40 GPa, 30 GPa, 20 GPa, or anywhere in between.

Stiffening Heat Treatment

Optionally, at least a second portion of the variably flexible (i.e., variably stiff) metal alloy (e.g., second portion 120 in FIG. 1) can be subjected to a stiffening heat treatment, as described above, to increase the elastic modulus of the second portion(s) by inducing a phase change from the β-phase to the α-phase or the ω-phase. Heat treating the at least second portion 120 can be performed by induction heating, laser heating, resistive heating, furnace heating, or any other suitable heating or any combination thereof.

In one non-limiting example, the stiffening heat treatment can be performed at a temperature of from approximately 150° C. to approximately 400° C. (e.g., approximately 150° C., approximately 175° C., approximately 200° C., approximately 225° C., approximately 250° C., approximately 275° C., approximately 300° C., approximately 325° C., approximately 350° C., approximately 375° C., approximately 400° C., or anywhere in between) for a time period of approximately 30 minutes to approximately 168 hours (h) (i.e., 7 days). For example, a stiffening heat treatment at a temperature of between approximately 150° C. and approximately 400° C. can be performed for approximately 30 minutes, approximately 1 h, approximately 2 h, approximately 3 h, approximately 4 h, approximately 5 h, approximately 6 h, approximately 12 h, approximately 18 h, approximately 24 h, approximately 30 h, approximately 36 h, or approximately 72 h, approximately 5 days, or approximately 7 days). For example, heat treating the second portion 120 of the intermediary alloy can be performed for approximately 6 h, approximately 7 h, approximately 8 h, approximately 9 h, approximately 10 h, approximately 11 h, approximately 12 h, approximately 13 h, approximately 14 h, approximately 15 h, approximately 16 h, approximately 17 h, approximately 18 h, approximately 19 h, approximately 20 h, approximately 21 h, approximately 22 h, approximately 23 h, approximately 24 h, approximately 30 h, approximately 36 h, approximately 42 h, approximately 48 h, approximately 54 h, approximately 60 h, approximately 66 h, approximately 72 h, approximately 84 h, approximately 96 h, approximately 108 h, approximately 120 h, approximately 132 h, approximately 144 h, approximately 156 h, approximately 168 h, or anywhere in between. Applying stiffening heat treatment at a temperature between approximately 150° C. and approximately 400° C. of about 15 minutes to about 600 minutes can stiffen the portion of the variably flexible (i.e., variably stiff) metal alloy by inducing a phase change from the β-phase to the ω-phase. Performing the stiffening heat treatment in this manner can increase the stiffness, providing an increased elastic modulus up to about 90 GPa (e.g., increasing the elastic modulus from the intermediate elastic modulus of about 60 GPa-80 GPa up to an increased elastic modulus of about 90 GPa).

In another non-limiting example, the stiffening heat treatment can be performed at a temperature of from approximately 400° C. to approximately 650° C. (e.g., approximately 400° C., approximately 410° C., approximately 420° C., approximately 430° C., approximately 440° C., approximately 450° C., approximately 460° C., approximately 470° C., approximately 480° C., approximately 490° C., approximately 500° C., approximately 510° C., approximately 520° C., approximately 530° C., approximately 540° C., approximately 550° C., approximately 560° C., approximately 570° C., approximately 580° C., approximately 590° C., approximately 600° C., approximately 610° C., approximately 620° C., approximately 630° C., approximately 640° C., approximately 650° C., or anywhere in between) for a time period of approximately 6 hours (h) to approximately 168 hours (i.e., 7 days) (e.g., for approximately 6 h, approximately 12 h, approximately 18 h, approximately 24 h, approximately 30 h, approximately 36 h, or approximately 72 h, approximately 5 days, or approximately 7 days). For example, heat treating the second portion 120 of the intermediary alloy can be performed for approximately 6 h, approximately 7 h, approximately 8 h, approximately 9 h, approximately 10 h, approximately 11 h, approximately 12 h, approximately 13 h, approximately 14 h, approximately 15 h, approximately 16 h, approximately 17 h, approximately 18 h, approximately 19 h, approximately 20 h, approximately 21 h, approximately 22 h, approximately 23 h, approximately 24 h, approximately 30 h, approximately 36 h, approximately 42 h, approximately 48 h, approximately 54 h, approximately 60 h, approximately 66 h, approximately 72 h, approximately 84 h, approximately 96 h, approximately 108 h, approximately 120 h, approximately 132 h, approximately 144 h, approximately 156 h, approximately 168 h, or anywhere in between. Performing the stiffening heat treatment at a temperature of from approximately 400° C. to approximately 650° C. for a time period of approximately 6 hours (h) to approximately 7 days (i.e., 168 h) can increase a stiffness of the portion subjected to the stiffening heat treatment by inducing a phase change in the metal alloy from the β-phase to the α-phase. Performing the stiffening heat treatment in this manner can increase the stiffness of the at least second portion. Specifically, the stiffening heat treatment can increase the elastic modulus from the intermediate elastic modulus (e.g., about 60 GPa-about 80 GPa) to an increased elastic modulus up to about 110 GPa (e.g., about 90 GPa, about 100 GPa, about 110 GPa, or anywhere in between).

In some examples, as described above, portions of the metal alloy not subjected to the stiffening heat treatment can be thermally insulated or chilled as described above to prevent unintentional heat treating of the portions of the metal alloy not being subjected to the stiffening heat treatment.

In some cases, the metal alloy is not subjected to the stiffening heat treatment. If the at least second portion is not subjected to stiffening heat treatment, the at least second portion can have an elastic modulus that is similar to or the same as the intermediate elastic modulus of the as-cast metal alloy (e.g., having an elastic modulus of about 60 GPa to about 80 GPa), and thus have an elastic modulus that is greater than the elastic modulus of the at least first portion (e.g., first portions 110, 130) after being subjected to the softening heat treatment and subsequent loading.

Method B

Provided herein is a second exemplary method of making a variably elastic metal alloy article, such as an article formed from the alloys disclosed above. The method includes (i) casting a metal alloy, homogenizing the metal alloy, and cooling the cast metal alloy as described above, (ii) heat treating the cast metal alloy to slightly strengthen the cast metal alloy, (iii) heat treating at least a first portion of the metal alloy to train the first portion (e.g., the softening heat treatment as described above), and (iv) optionally heat treating at least a second portion of the metal alloy to increase an elastic modulus of the at least second portion (e.g., the stiffening heat treatment as described above). In some cases, the method includes thermally insulating or chilling portions of the metal alloy not subjected to heat treating.

Strengthening Heat Treatment

In some examples, an initial strengthening heat treatment can be performed at a temperature of from approximately 150° C. to approximately 400° C. (e.g., approximately 150° C., approximately 175° C., approximately 200° C., approximately 225° C., approximately 250° C., approximately 275° C., approximately 300° C., approximately 325° C., approximately 350° C., approximately 375° C., approximately 400° C., or anywhere in between) for a time period of approximately 30 minutes to approximately 168 hours (h) (i.e., 7 days) (e.g., for approximately 30 minutes, approximately 1 h, approximately 2 h, approximately 3 h, approximately 4 h, approximately 5 h, approximately 6 h, approximately 12 h, approximately 18 h, approximately 24 h, approximately 30 h, approximately 36 h, or approximately 72 h, approximately 5 days, or approximately 7 days). For example, heat treating the second portion 120 of the intermediary alloy can be performed for approximately 6 h, approximately 7 h, approximately 8 h, approximately 9 h, approximately 10 h, approximately 11 h, approximately 12 h, approximately 13 h, approximately 14 h, approximately 15 h, approximately 16 h, approximately 17 h, approximately 18 h, approximately 19 h, approximately 20 h, approximately 21 h, approximately 22 h, approximately 23 h, approximately 24 h, approximately 30 h, approximately 36 h, approximately 42 h, approximately 48 h, approximately 54 h, approximately 60 h, approximately 66 h, approximately 72 h, approximately 84 h, approximately 96 h, approximately 108 h, approximately 120 h, approximately 132 h, approximately 144 h, approximately 156 h, approximately 168 h, or anywhere in between. In some examples, performing the strengthening heat treatment at a temperature of between approximately 150° C. and approximately 400° C. for a time period of about 60 minutes to about 300 minutes can create a non-uniform ω-phase in the metal alloy (e.g., the entire alloy does not undergo a complete phase change to the ω-phase). Creating the ω-phase in the metal alloy blocks the phase change from the β-phase to the α"-phase that can occur after a subsequent softening heat treatment and loading. Thus, the areas of the metal alloy that undergo a phase change to the ω-phase are prevented from undergoing the phase change from the β-phase to the α"-phase after a subsequent softening heat treatment and loading. Areas of the metal alloy that do not undergo a phase change to the ω-phase can change to α"-phase after a softening heat treatment and subsequent loading as described above.

Softening Heat Treatment

As described above, after strengthening, at least a first portion of the metal alloy (e.g., first portions 110, 130 in FIG. 1) can be subjected to softening heat treatment and subsequent loading to induce a phase change of the at least first portion from the β-phase to the α"-phase, decreasing the stiffness of the at least first portion. Heat treating the at least first portion can be performed by induction heating, laser heating, resistive heating, furnace heating, or any other suitable heating or any combination thereof.

In some examples, the softening heat treatment can be performed at a temperature of from about 150° C. to about 1200° C. (e.g., about 250° C., about 750° C., about 1100° C., or about 600° C.). For example, the softening heat treatment can be performed at a temperature of about 150° C., 175° C., 200° C., 225° C., 250° C., 275° C., 300° C., 325° C., 350° C., 375° C., 400° C., 425° C., 450° C., 475° C., 500° C., 525° C., 550° C., 575° C., 600° C., 625° C., 650° C., 675° C., 700° C., 725° C., 750° C., 775° C., 800° C., 825° C., 850° C., 875° C., 900° C., 925° C., 950° C., 975° C., 1000° C., 1025° C., 1050° C., 1075° C., 1100° C., 1125° C., 1150° C., 1175° C., 1200° C., or anywhere in between. The softening heat treatment can be performed from about 1 minute to about 15 minutes (e.g., 5 minutes, 10 minutes, or 15 minutes). For example, the softening heat treatment can be performed for about 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, or anywhere in between, up to a limit (e.g., about 15 minutes). Up to the limit, increasing the duration of heat treatment will reduce the stiffness of the at least first portion after subsequent loading. In some examples, heat treating the at least first portion and subjecting the alloy to loading in the described manner can decrease the stiffness of the at least first portion from the intermediate stiffness to a decreased stiffness, having elastic modulus values down to about 40 to about 20 GPa. For example, the decreased elastic modulus can be about 40 GPa, 30 GPa, 20 GPa, or anywhere in between.

As mentioned above, all portions except the at least first portion subjected to the softening heat treatment (e.g., the at least second portion such as second portion 120) can be thermally insulated during the softening heat treatment to prevent any proximal heat treating of the at least second portion.

Stiffening Heat Treatment

Optionally, at least a second portion of the variably elastic metal alloy (e.g., second portion 120 in FIG. 1) is subjected to the stiffening heat treatment to increase the elastic modulus of the at least second portion relative to the remainder of the metal alloy by inducing a phase change from the β-phase to the α-phase and/or the ω-phase. Heat treating the at least second portion can be performed by induction heating, laser heating, resistive heating, furnace heating, or any other suitable heating or any combination thereof.

In some non-limiting examples, the stiffening heat treatment can be performed at a temperature from approximately 400° C. to approximately 650° C. (e.g., approximately 400° C., approximately 410° C., approximately 420° C., approximately 430° C., approximately 440° C., approximately 450° C., approximately 460° C., approximately 470° C., approximately 480° C., approximately 490° C., approximately 500° C., approximately 510° C., approximately 520° C., approximately 530° C., approximately 540° C., approximately 550° C., approximately 560° C., approximately 570° C., approximately 580° C., approximately 590° C., approximately 600° C., approximately 610° C., approximately 620° C., approximately 630° C., approximately 640° C., approximately 650° C., or anywhere in between) for a time period of approximately 6 hours to approximately 7 days (i.e., 168 hours). For example, the stiffening heat treatment can be performed at a temperature of from approximately 400° C. to approximately 650° C. for a time period of about 6 h, about 7 h, about 8 h, about 9 h, about 10 h, about 11 h, about 12 h, about 13 h, about 14 h, about 15 h, about 16 h, about 17 h, about 18 h, about 19 h, about 20 h, about 21 h, about 22 h, about 23 h, about 24 h, about 30 h, about 36 h, about 42 h, about 48 h, about 54 h, about 60 h, about 66 h, about 72 h, about 84 h, about 96 h, about 108 h, about 120 h, about 132 h, about 144 h, about 156 h, about 168 h, or anywhere in between. Performing the stiffening heat treatment at a temperature of from approximately 400° C. to approximately 650° C. for a time period of approximately 6 hours to approximately 168 hours can create the α-phase and/or the ω-phase, providing a higher stiffness metal alloy. For example, the α-phase metal alloy can have an increased elastic modulus of from about 90 GPa to about 110 GPa (e.g., about 90 GPa, about 100 GPa, about 110 GPa, or anywhere in between). In some examples, the ω-phase metal alloy can have an increased elastic modulus of up to about 90 GPa.

In some examples, any portion of the metal alloy not subjected to the stiffening heat treatment can be thermally insulated as described above to prevent unintentional heat treating of the portions of the metal alloy not being subjected to the stiffening heat treatment.

As described above, in some cases, the at least second portion (e.g., second portion 120) is not subjected to stiffening heat treatment. If the at least second portion is not subjected to stiffening heat treatment, the at least second portion can have a stiffness that is similar to or the same as the intermediate stiffness of the as-cast metal alloy (e.g., having an elastic modulus of about 60 GPa to about 80 GPa), and thus have an elastic modulus that is greater than the elastic modulus of the at least first portion (e.g., first portions 110, 130) after it is subjected to the softening heat treatment and subsequent loading.

Optional Methods

In addition to the methods described above, including (i) casting a metal alloy and cooling the cast metal alloy, (ii) optionally cold working the cast metal alloy, (iii) heat treating at least a first portion of the metal alloy to decrease an elastic modulus of the first portion (e.g., the softening heat treatment as described above), and (iv) optionally heat treating at least a second portion of the metal alloy to increase a modulus of elasticity of the at least second portion (e.g., the stiffening heat treatment as described above), and, in some cases, (v) thermally insulating portions of the metal alloy not subjected to heat treating, the alloys described herein can be subjected to an optional tuning heat treatment to tune an elastic modulus of the at least first portion subjected to the softening heat treatment.

Tuning Heat Treatment

In some non-limiting examples, a tuning heat treatment step is employed to stiffen one or more portions of the metal alloy after the softening heat treatment described above (e.g., to slightly strengthen a softened portion of the metal alloy) to fine tune the elastic modulus. In some cases, the tuning heat treatment can be performed at a temperature of from approximately 150° C. to approximately 400° C. (e.g., approximately 150° C., approximately 175° C., approximately 200° C., approximately 225° C., approximately 250° C., approximately 275° C., approximately 300° C., approximately 325° C., approximately 350° C., approximately 375° C., approximately 400° C., or anywhere in between) for approximately 30 minutes to approximately 168 hours (h) (i.e., 7 days) (e.g., for approximately 30 minutes, approximately 1 h, approximately 2 h, approximately 3 h, approximately 4 h, approximately 5 h, approximately 6 h, approximately 12 h, approximately 18 h, approximately 24 h, approximately 30 h, approximately 36 h, or approximately 72 h, approximately 5 days, or approximately 7 days). For example, heat treating the second portion 120 of the intermediary alloy can be performed for approximately 6 h, approximately 7 h, approximately 8 h, approximately 9 h, approximately 10 h, approximately 11 h, approximately 12 h, approximately 13 h, approximately 14 h, approximately 15 h, approximately 16 h, approximately 17 h, approximately 18 h, approximately 19 h, approximately 20 h, approximately 21 h, approximately 22 h, approximately 23 h, approximately 24 h, approximately 30 h, approximately 36 h, approximately 42 h, approximately 48 h, approximately 54 h, approximately 60 h, approximately 66 h, approximately 72 h, approximately 84 h, approximately 96 h, approximately 108 h, approximately 120 h, approximately 132 h, approximately 144 h, approximately 156 h, approximately 168 h, or anywhere in between. Performing the tuning heat treatment in this manner can create a small amount of the ω-phase in the softened portion of the metal alloy. The small amount of the ω-phase in the softened portion of the metal alloy can be positioned at localized points throughout the metal alloy (i.e., the ω-phase is inconsistent throughout the metal alloy). Creating an inconsistent ω-phase throughout the metal alloy can partially prevent the phase change from the β-phase to the α"-phase possible after softening heat treatment, thus providing an increased stiffness in the softened portion of the metal alloy. The amount of ω-phase created can be controlled by changing the time and/or temperature of the tuning heat treatment. For example, increasing the heating temperature and/or time can increase the amount of ω-phase, and vice versa. The tuning heat treatment can increase the decreased stiffness of the softened portion of the metal alloy, providing a tuning of the elastic modulus of the softened portion of the metal alloy (e.g., from about 20 GPa to about 40 GPa) up to about 90 GPa. For example, the tuning heat treatment can increase the decreased elastic modulus of the softened portion of the metal alloy to about 30 GPa, 40 GPa, 50 GPa, 60 GPa, 70 GPa, 80 GPa, 90 GPa, or anywhere in between.

Methods of Using

The alloys and methods described herein can be used in any suitable application, including but not limited to, medical implants and medical device applications. For example, the exemplary alloys described herein can be used as spinal rods for degeneration and deformity corrections in both children and adults, fracture stabilization devices including plates or intramedullary nails, stems of hip, knee, shoulder, and hand/foot joint replacements, spinal interbody cages, endoprostheses, and dental implants.

For example, the disclosed alloys can be used to provide a spinal rod that has more flexibility towards its ends to reduce the stress on bone and screw anchors, but greater rigidity in its center to maintain curve correction for treating scoliosis. In some examples, the disclosed alloys can be provided as spinal rods having optimal stiffness and flexibility that can be tailored to individual patients as described in U.S. Provisional Application No. 62/515,390 filed on Jun. 5, 2017 and titled "Self-Adaptive Growing Rod for the Treatment of Pediatric Scoliosis," the contents of which are incorporated herein by this reference. In some examples, the disclosed alloys can alleviate anchor failure in a growing spinal rod, allowing the growing spinal rod to remain attached to the spine. Additionally, TiNb alloys are biocompatible and corrosion resistant, providing growing spinal rods amenable to implantation.

In some aspects, the exemplary alloys described herein can be used in sporting goods, including but not limited to, fishing rods, tennis racquets, and golf clubs. The alloys and methods described herein can be used in transportation and automotive applications, such as but not limited to, aircraft, railway, automobile, or commercial vehicle applications. For example, the alloys could be used for chassis, crossmember, and intra-chassis components. In certain aspects, the alloys and methods can be used to prepare motor vehicle body part products. For example, the disclosed alloys and methods can be used to prepare automobile body parts, such as bumpers, side beams, roof beams, cross beams, pillar reinforcements (e.g., A-pillars, B-pillars, and C-pillars), inner panels, side panels, floor panels, tunnels, structure panels, reinforcement panels, inner hoods, or trunk lid panels. The disclosed aluminum alloys and methods can also be used in aircraft or railway vehicle applications, to prepare, for example, external and internal panels.

Illustrations

As used below, any reference to a series of illustrations is to be understood as a reference to each of those illustrations disjunctively (e.g., "Illustrations 1-4" is to be understood as "Illustrations 1, 2, 3, or 4").

Illustration 1 is a method of making a variably elastic metal alloy product comprising: casting a metal alloy, wherein after casting the metal alloy has an intermediate elastic modulus; heat treating at least a first portion of the metal alloy to train the at least first portion such that, when subjected to subsequent loading, the at least first portion has a decreased elastic modulus that is lower than the intermediate elastic modulus; and thermally insulating any portion not subjected to heat treating to maintain the intermediate elastic modulus of the any portion not subjected to heat treating.

Illustration 2 is the method of any preceding or subsequent illustration, wherein casting the metal alloy comprises vacuum arc melting, vacuum induction melting, or skull melting.

Illustration 3 is the method of any preceding or subsequent illustration, wherein casting the metal alloy provides a metal alloy comprising at least about 70% beta-phase crystalline structure.

Illustration 4 is the method of any preceding or subsequent illustration, further comprising cooling the cast metal alloy.

Illustration 5 is the method of any preceding or subsequent illustration, wherein cooling is performed at a rate sufficient to maintain the at least about 70% beta-phase crystalline structure.

Illustration 6 is the method of any preceding or subsequent illustration, further comprising cold working the metal alloy after casting.

Illustration 7 is the method of any preceding or subsequent illustration, wherein cold working the metal alloy comprises cold rolling, wire drawing, extrusion, or swaging.

Illustration 8 is the method of any preceding or subsequent illustration, wherein cold working the metal alloy further comprises cold rolling the metal alloy to at least a 25% reduction in thickness of the metal alloy.

Illustration 9 is the method of any preceding or subsequent illustration, wherein cold working further comprises wire drawing, extruding or swaging to at least a 25% reduction in cross-sectional area of the metal alloy.

Illustration 10 is the method of any preceding or subsequent illustration, wherein heat treating the at least first portion of the metal alloy trains the at least first portion such that the at least first portion undergoes a stress induced phase transformation from a beta-phase to an alpha"-phase crystalline structure when subjected to the subsequent loading.

Illustration 11 is the method of any preceding or subsequent illustration, wherein heat treating at least the first portion of the metal alloy is performed at a temperature from approximately 150° C. and approximately 1200° C.

Illustration 12 is the method of any preceding or subsequent illustration, wherein heat treating at least the first portion of the metal alloy is performed at approximately 600° C.

Illustration 13 is the method of any preceding or subsequent illustration, wherein heat treating at least the first portion of the metal alloy is performed for approximately 1 minute to approximately 20 minutes.

Illustration 14 is the method of any preceding or subsequent illustration, wherein heat treating at least the first portion of the metal alloy is performed for approximately 15 minutes.

Illustration 15 is the method of any preceding or subsequent illustration, wherein thermally insulating any portion not subjected to heat treating to maintain an elastic modulus of the portion not subjected to heat treating comprises direct contact chilling, air cooling, or gas flow cooling.

Illustration 16 is the method of any preceding or subsequent illustration, further comprising heat treating at least a second portion of the metal alloy to obtain an increased elastic modulus of the at least second portion, wherein the increased elastic modulus is greater than the intermediate elastic modulus.

Illustration 17 is the method of any preceding or subsequent illustration, wherein heat treating at least the second portion of the metal alloy is performed from approximately 400° C. to approximately 650° C.

Illustration 18 is the method of any preceding or subsequent illustration, wherein heat treating at least the second portion of the metal alloy is performed between approximately 6 hours and approximately 168 hours.

Illustration 19 is the method of any preceding or subsequent illustration, wherein heat treating the at least second portion of the metal alloy to obtain the increased modulus of elasticity of the second portion comprises a phase change from a beta-phase to an alpha-phase crystalline structure.

Illustration 20 is the method of any preceding or subsequent illustration, wherein heat treating at least the second portion of the metal alloy is performed from approximately 150° C. to approximately 400° C.

Illustration 21 is the method of any preceding or subsequent illustration, wherein heat treating at least the second portion of the metal alloy is performed between approximately 30 minutes and approximately 168.

Illustration 22 is the method of any preceding or subsequent illustration, wherein heat treating the at least second portion of the metal alloy to obtain the increased modulus of elasticity of the second portion comprises a stress induced phase transformation from the beta-phase to an omega-phase crystalline structure.

Illustration 23 is the method of any preceding or subsequent illustration, wherein heat treating comprises at least one of induction heating, laser heating, resistive heating, and furnace heating.

Illustration 24 is a method of making a variably elastic metal alloy product according to any preceding or subsequent illustration, comprising: casting a metal alloy, wherein casting the metal alloy provides a metal alloy having an intermediate elastic modulus; heat treating the metal alloy to strengthen the metal alloy; heat treating at least a first portion of the metal alloy to train the at least first portion such that, when subjected to subsequent loading, the at least first portion has a decreased elastic modulus that is less than the intermediate elastic modulus; and thermally insulating any portion not subjected to heat treating to maintain the intermediate elastic modulus of the any portion not subjected to heat treating.

Illustration 25 is the method of any preceding or subsequent illustration, wherein casting the metal alloy comprises vacuum arc melting, vacuum induction melting, or skull melting.

Illustration 26 is the method of any preceding or subsequent illustration, wherein casting the metal alloy further provides a metal alloy comprising at least about 70% beta-phase crystalline structure.

Illustration 27 is the method of any preceding or subsequent illustration, further comprising cooling the cast metal alloy.

Illustration 28 is the method of any preceding or subsequent illustration, wherein the cooling is performed at a rate sufficient to maintain the at least about 70% beta-phase crystalline structure.

Illustration 29 is the method of any preceding or subsequent illustration, wherein heat treating the metal alloy to strengthen the metal alloy comprises creating an inconsistent omega-phase crystalline structure.

Illustration 30 is the method of any preceding or subsequent illustration, wherein heat treating the metal alloy to strengthen the metal alloy is performed at a temperature from approximately 150° C. and approximately 400° C.

Illustration 31 is the method of any preceding or subsequent illustration, wherein heat treating at least the first portion of the metal alloy is performed for approximately 30 minutes to approximately 168 hours.

Illustration 32 is the method of any preceding or subsequent illustration, wherein heat treating at least the first portion of the metal alloy to train the at least first portion is performed at a temperature from approximately 400° C. and approximately 1200° C.

Illustration 33 is the method of any preceding or subsequent illustration, wherein heat treating at least the first portion of the metal alloy to train the at least first portion is performed for approximately 1 minute to approximately 15 minutes.

Illustration 34 is the method of any preceding or subsequent illustration, wherein thermally insulating any portion not subjected to heat treating to maintain the intermediate elastic modulus of the portion not subjected to heat treating comprises direct contact chilling, air cooling, or gas flow cooling.

Illustration 35 is the method of any preceding or subsequent illustration, further comprising heat treating at least a second portion of the metal alloy to obtain an increased elastic modulus of the at least second portion.

Illustration 36 is the method of any preceding or subsequent illustration, wherein heat treating at least the second portion of the metal alloy is performed from approximately 400° C. to approximately 650° C.

Illustration 37 is the method of any preceding or subsequent illustration, wherein heat treating at least the second portion of the metal alloy is performed between approximately 6 hours and approximately 168 hours.

Illustration 38 is the method of any preceding or subsequent illustration, wherein heat treating the at least second portion of the metal alloy to obtain the increased modulus of elasticity comprises a phase change from the beta-phase to an alpha-phase crystalline structure or an omega-phase crystalline structure.

Illustration 39 is the method of any preceding or subsequent illustration, wherein heat treating comprises at least one of induction heating, laser heating, resistive heating, and furnace heating.

Illustration 40 is the method of any preceding or subsequent illustration, further comprising tuning heat treating the metal alloy.

Illustration 41 is the method of any preceding or subsequent illustration, wherein tuning heat treating the metal alloy is performed at a temperature of from approximately 150° C. to approximately 400° C.

Illustration 42 is the method of any preceding or subsequent illustration, wherein tuning heat treating the metal alloy is performed for approximately 30 minutes to approximately 168 hours.

Illustration 43 is the method of any preceding or subsequent illustration, wherein tuning heat treating the metal alloy comprises creating an omega-phase crystalline structure.

Illustration 44 is a variably elastic metal alloy product according to any preceding or subsequent illustration, comprising 70 atomic percent (at. %) to 78 at. % Ti, 18 at. % to 24 At. % Nb, up to 12 at. % of a third alloying element selected from the group consisting of zirconium (Zr), tin (Sn), chromium (Cr), molybdenum (Mo), iron (Fe), and tantalum (Ta), and up to 1 at. % of impurities, wherein the variably elastic metal alloy product comprises at least a rigid portion and at least a flexible portion when subjected to a load.

Illustration 45 is the variably elastic metal alloy product of any preceding or subsequent illustration, further comprising a plurality of rigid portions and a plurality of flexible portions when subjected to the load.

Illustration 46 is the variably elastic metal alloy product of any preceding or subsequent illustration, wherein the rigid portion has an elastic modulus of from approximately 80 GPa to approximately 110 GPa.

Illustration 47 is the variably elastic metal alloy product of any preceding or subsequent illustration, wherein the flexible portion has an elastic modulus of from approximately 20 GPa to approximately 40 GPa when subjected to the load.

Illustration 48 is the variably elastic metal alloy product of any preceding or subsequent illustration, wherein the plurality of rigid portions and the plurality of flexible portions are controllably distributed across the variably elastic metal alloy product.

Illustration 49 is the variably elastic metal alloy product of any preceding or subsequent illustration, wherein the variably elastic metal alloy product is a medical device, a medical implant, a sporting good, a transportation structural part, an automotive structural part, an automotive aesthetic part, an aerospace structural part, or an aerospace aesthetic part.

Illustration 50 is a variably elastic metal alloy product according to any preceding or subsequent illustration, comprising 72 atomic percent (at. %) to 78 at. % Ti, 22 at. % to 28 At. % Nb, and up to 1 at. % of impurities, wherein the variably elastic metal alloy product comprises at least a rigid portion and at least a flexible portion when subjected to a load.

Illustration 51 is the variably elastic metal alloy product of any preceding or subsequent illustration, further comprising a plurality of rigid portions and a plurality of flexible portions when subjected to the load.

Illustration 52 is the variably elastic metal alloy product of any preceding or subsequent illustration, wherein the rigid portion has an elastic modulus of from approximately 80 GPa to approximately 110 GPa.

Illustration 53 is the variably elastic metal alloy product of any preceding or subsequent illustration, wherein the flexible portion has an elastic modulus of from approximately 20 GPa to approximately 40 GPa when subjected to the load.

Illustration 54 is the variably elastic metal alloy product of any preceding or subsequent illustration, wherein the plurality of rigid portions and the plurality of flexible portions are controllably distributed across the variably elastic metal alloy product.

Illustration 55 is the variably elastic metal alloy product of any preceding or subsequent illustration, wherein the variably elastic metal alloy product is a medical device, a medical implant, a sporting good, a transportation structural part, an automotive structural part, an automotive aesthetic part, an aerospace structural part, or an aerospace aesthetic part.

Illustration 56 is a variably elastic metal alloy spinal implant according to any preceding or subsequent illustration, comprising 70 atomic percent (at. %) to 78 at. % Ti, 18 at. % to 24 At. % Nb, up to 12 at. % of a third alloying element selected from the group consisting of zirconium (Zr), tin (Sn), chromium (Cr), molybdenum (Mo), iron (Fe), and tantalum (Ta), and up to 1 at. % of impurities, wherein the variably elastic metal alloy spinal implant comprises a rigid portion between two flexible ends when subjected to a load.

EXAMPLES

Figure 2:
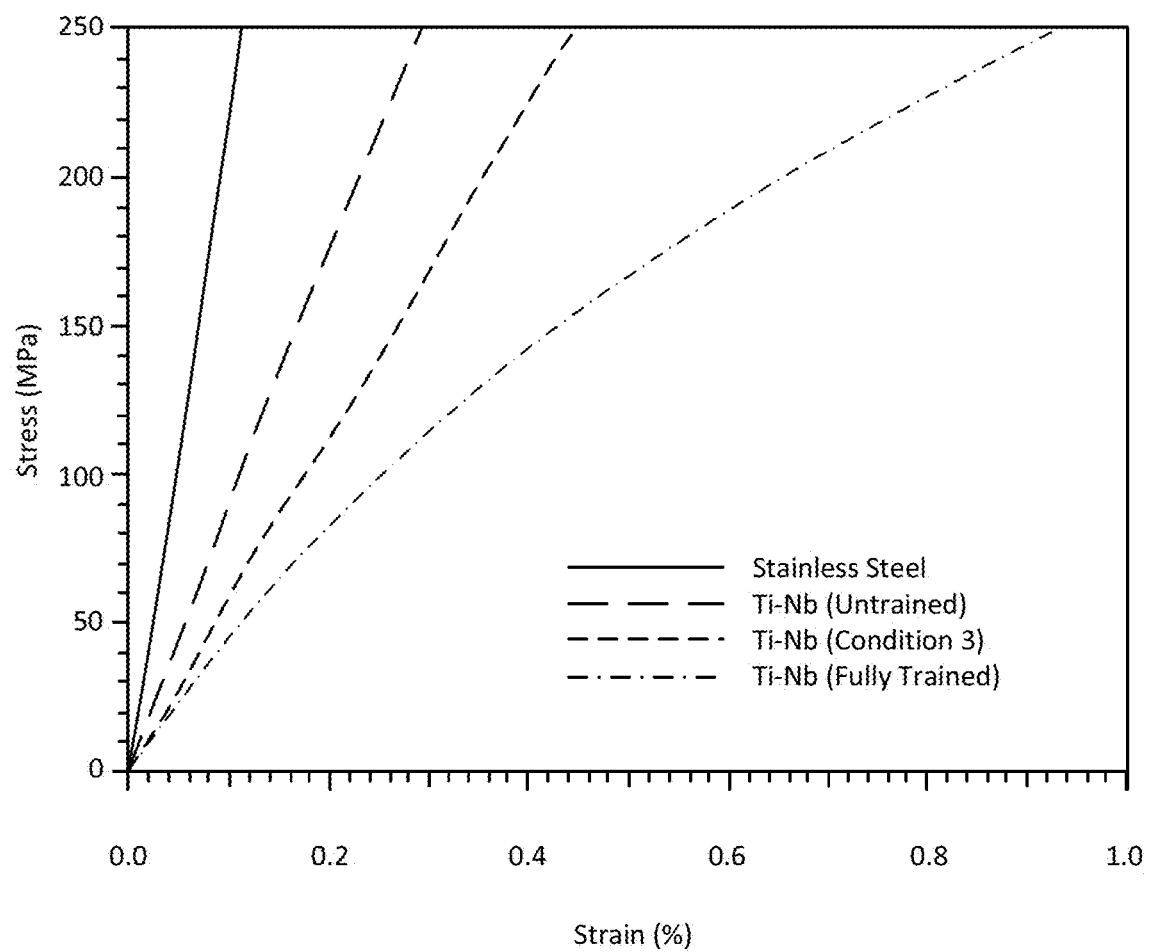
FIG. 2 is a graph of stress versus strain of comparative alloys and an exemplary alloy according to certain aspects of the present disclosure.

In some non-limiting examples, the methods described above can provide a variably flexible (i.e., variably stiff) alloy article. Specifically, employing the methods described above can be used to tune an elastic modulus (i.e., stiffness) of an alloy article at various locations along a length of a single alloy article. FIG. 2 shows a graph of tensile test results of comparative alloys versus exemplary alloys as described herein. Strain (%) is shown on the x-axis while stress (MPa) is shown on the y-axis. In particular, the comparative alloy is a stainless steel alloy (solid line), and the exemplary alloys are an Untrained (i.e., as-cast) TiNb alloy, a TiNb alloy in Condition 3 as described below and a Fully Trained TiNb alloy. The exemplary TiNb alloys exhibit a dynamic elastic modulus wherein increasing strain can initially require increasing stress up to a point and then further straining requires a reduced increase in applied stress. Evident in the graph, changes in elastic moduli of the exemplary alloys are nonlinear changes. Incremental changes in the elastic modulus can indicate how strain changes with changes in applied stress.

Figure 3:
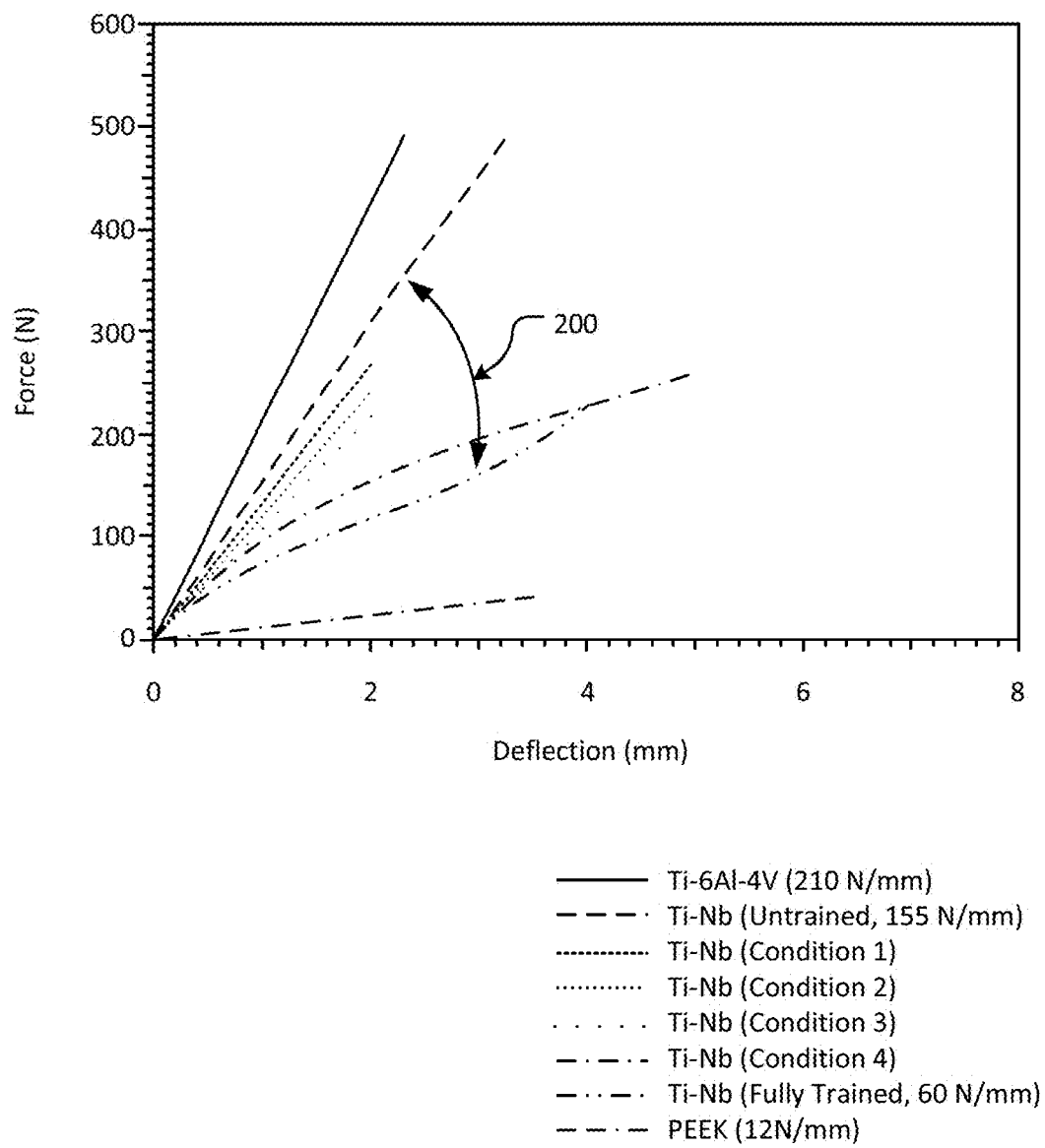
FIG. 3 is a graph of load-deflection response of a comparative alloy, a comparative polymer, and an exemplary alloy according to certain aspects of the present disclosure.

FIG. 3 is a graph showing a load-deflection response of a comparative Ti-6Al-4V alloy rod having a circular cross-section with a 5.5 mm diameter, a comparative polyetherether ketone (PEEK) polymer rod having a circular cross-section with a 6.3 mm diameter, and six (6) exemplary $Ti_{75}Nb_{25}$ alloy rods subjected to a 60% reduction in cross-sectional area having a circular cross-sectional diameter of 5.5 mm. Force (N) is illustrated on the y-axis and deflection (mm) is illustrated on the x-axis. Selective portions of the 6 exemplary $Ti_{75}Nb_{25}$ alloy rods were heat treated at about 600° C. for various times ranging from 0 minutes (i.e., an unprocessed alloy, referred to as "Untrained") to about 15 minutes (referred to as "Fully Trained"). The load deflection response was performed by a three-point bending test having a span length of about 100 mm at a temperature of about room temperature.

The graph of FIG. 3 illustrates that varying heat treatment time can provide different elastic moduli in the exemplary alloy. Comparative samples (e.g., Ti-6Al-4V alloy and a) and exemplary TiNb alloy samples were subjected to a three-point bend test in accordance with ASTM Standard F2193. The elastic modulus of the exemplary $Ti_{75}Nb_{25}$ alloy can vary from about 25% to 80% of the comparative Ti-6Al-4V alloy rod. For example, the comparative Ti-6Al-4V alloy rod exhibited a stiffness of 210 Newtons per millimeter (N/mm) and a Fully Trained exemplary $Ti_{75}Nb_{25}$ alloy rod exhibited a stiffness of 60 N/mm (i.e., the Fully Trained exemplary $Ti_{75}Nb_{25}$ alloy rod exhibited a stiffness of about 28.6% of the comparative Ti-6Al-4V alloy rod). The Fully Trained TiNb alloy rod refers to a TiNb alloy subjected to cold working to a 60% reduction in cross sectional area (e.g., a final diameter of 5.5 mm) and a heat treatment of 600° C. for 15 minutes. In some further examples, an Untrained (i.e., as-cast) exemplary $Ti_{75}Nb_{25}$ alloy rod exhibited a stiffness of 155 N/mm (i.e., the exemplary Untrained $Ti_{75}Nb_{25}$ alloy rod exhibited a stiffness of about 73.8% of the comparative Ti-6Al-4V alloy rod). In some cases, varying the heat treatment time can provide a range 200 (see FIG. 3) of achievable elastic moduli for the exemplary $Ti_{75}Nb_{25}$ alloy. Untrained refers to a TiNb alloy subjected to cold working to a 60% reduction in cross sectional area (e.g., a final diameter of 5.5 mm) and no heat treatment. Condition 1 refers to a TiNb alloy subjected to cold working to a 60% reduction in cross sectional area (e.g., a final diameter of 5.5 mm) and a heat treatment of 600° C. for 1 minute. Condition 1 provided a TiNb alloy with a stiffness of 134 N/mm. Condition 2 refers to a TiNb alloy subjected to cold working to a 60% reduction in cross sectional area (e.g., a final diameter of 5.5 mm) and a heat treatment of 600° C. for 2 minutes. Condition 2 provided a TiNb alloy with a stiffness of 119 N/mm. Condition 3 refers to a TiNb alloy subjected to cold working to a 60% reduction in cross sectional area (e.g., a final diameter of 5.5 mm) and a heat treatment of 600° C. for 5 minutes. Condition 3 provided a TiNb alloy with a stiffness of 112 N/mm. Condition 4 refers to a TiNb alloy subjected to cold working to a 60% reduction in cross sectional area (e.g., a final diameter of 5.5 mm) and a heat treatment of 600° C. for 10 minutes. Condition 4 provided a TiNb alloy with a stiffness of 76 N/mm. "Fully Trained" refers to a TiNb alloy subjected to cold working to a 60% reduction in cross sectional area (e.g., a final diameter of 5.5 mm) and a heat treatment of 600° C. for 15 minutes. The comparative PEEK rod having a diameter of 6.3 mm exhibited a stiffness of 12 N/mm.

Figure 4:
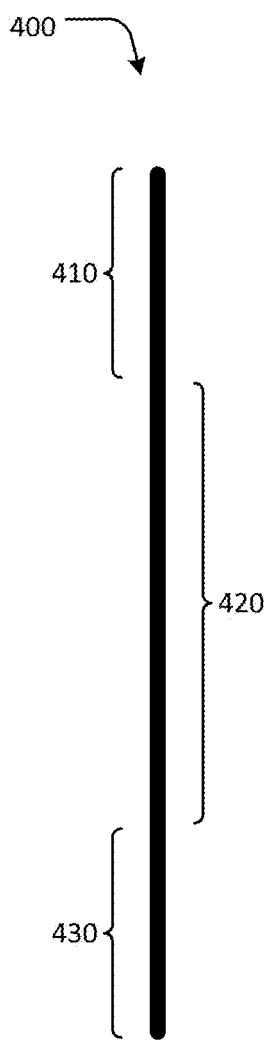
FIG. 4 is a schematic illustration of an exemplary alloy rod according to certain aspects of the present disclosure.

An exemplary alloy including 75 Ti, 25 Nb ($Ti_{75}Nb_{25}$), and up to about 1% impurities was cast from vacuum arc melting into a rod 400 as shown in FIG. 4. The cast $Ti_{75}Nb_{25}$ alloy was machined into a rod with a 10 mm diameter, and then cold swaged at room temperature to a longer rod having a 5.5 mm diameter. The swaged rod was straightened and heat treated at the ends only (e.g., see FIG. 4). Heat treating was performed at a temperature of 600° C. for 15 minutes in a tube furnace in air. A water chilled copper coil sleeve was fitted to a portion of the swaged rod where heat treatment was not desired (e.g., the second portion 420 in FIG. 4). The swaged rod having the water chilled copper coil sleeve was inserted into the tube furnace and heat treated for 15 minutes. Exposed areas (i.e., heated and non-chilled portions 410, 430) exhibited a lower elastic modulus in a three-point bending test, and the portion covered by the water chilled copper coil sleeve maintained a higher elastic modulus. The maximum temperature in the chilled area was measured to be approximately 55° C. using a thermocouple attached to the rod inside the water chilled copper coil sleeve.

Figure 5:
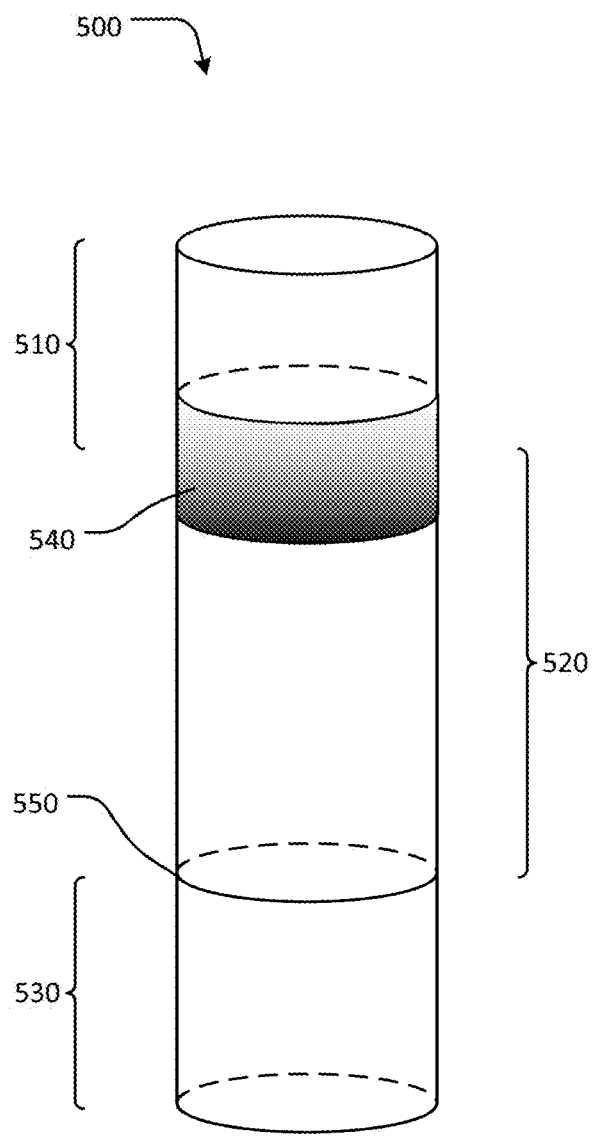
FIG. 5 is a schematic illustration of an exemplary alloy rod according to certain aspects of the present disclosure.

FIG. 5 shows a schematic of an exemplary alloy rod formed according to methods described herein. In some non-limiting examples, the exemplary alloy rod 500 can be selectively heat treated and chilled to provide a variably elastic alloy rod. A first portion 510 can be subjected to softening heat treatment according to methods described herein so that the first portion 510 has a first elastic modulus that is lower than it would be if not subjected to heat treatment and as compared with the remaining portions of the rod. Optionally, a second portion 520 of the exemplary alloy rod 500 can be subjected to stiffening heat treatment according to methods described herein such that the second portion 520 has a second elastic modulus that is higher than it would be if not subjected to the heat treatment and such that it is higher than the first elastic modulus. In some cases, a third portion 530 of the exemplary alloy rod 500 can be subjected to softening heat treatment according to methods described herein so that the third portion 530 has a third elastic modulus that is lower than it would be if not subjected to heat treatment and such that it is lower than the second elastic modulus. In some non-limiting examples, the exemplary alloy rod 500 can have a transition zone 540 such that a gradient exists between the first elastic modulus of the first portion 510 and the second elastic modulus of the second portion 520. A transition zone 540 can be tailored to specific applications, and in the present example is about 2 mm to about 3 mm. Transition zone 540 size can be tailored by selective chilling of any portion of the exemplary alloy rod 500 not subjected to heat treatment. In some cases, there can be a zero gradient transition zone 550 for example, between the second elastic modulus of the second portion 520 and the third elastic modulus of the third portion 530.

The foregoing description of the embodiments, including illustrated examples, has been presented only for the purpose of illustration and description and is not intended to be exhaustive or limiting to the precise forms disclosed. Numerous modifications, adaptations, and uses thereof will be apparent to those skilled in the art.

What we claim is:

1. A method of making a variably elastic metal alloy product comprising:
    casting a Ti-based metal alloy, wherein the cast Ti-based metal alloy has an intermediate elastic modulus and comprises at least about 70% beta-phase crystalline structure;
    heat treating at least one first portion of the Ti-based metal alloy to train the at least one first portion, wherein the heat treating results in a decreased elastic modulus that is lower than the intermediate elastic modulus or results in an increased elastic modulus that is higher than the intermediate elastic modulus; and
    during the heat treating at least one first portion, maintaining the intermediate elastic modulus of at least one second portion not subjected to heat treating,
    wherein the heat treating at least one first portion of the Ti-based metal alloy and the maintaining the intermediate elastic modulus of at least one second portion provide the variably elastic metal alloy product.

2. The method of claim 1, further comprising cooling the cast Ti-based metal alloy, wherein the cooling is performed at a rate sufficient to maintain the at least about 70% beta-phase crystalline structure.

3. The method of claim 1, further comprising cold working the Ti-based metal alloy after the casting and before the heat treating at least one first portion of the Ti-based metal alloy.

4. The method of claim 1, wherein the heat treating at least one first portion of the Ti-based metal alloy to result in the decreased elastic modulus trains the at least one first portion of the Ti-based metal alloy such that the at least one first portion of the Ti-based metal alloy undergoes a stress induced phase transformation from a beta-phase to an alpha"-phase crystalline structure.

5. The method of claim 3, wherein the heat treating at least one first portion of the Ti-based metal alloy to result in the decreased elastic modulus is performed at a temperature from approximately 150° C. to approximately 1200° C. for approximately 1 minute to approximately 20 minutes.

6. The method of claim 1, wherein the maintaining the intermediate elastic modulus of the at least one second portion not subjected to heat treating comprises thermally insulating, direct contact chilling, air cooling, or gas flow cooling the at least one second portion.

7. The method of claim 1, wherein the heat treating at least one first portion of the Ti-based metal alloy to result in the increased elastic modulus is performed from approximately 400° C. to approximately 650° C. for approximately 6 hours to approximately 168 hours.

8. The method of claim 7, wherein the heat treating at least one first portion of the Ti-based metal alloy to result in the increased elastic modulus comprises a phase change from a beta-phase to an alpha-phase crystalline structure, wherein the heat treating at least one first portion of the Ti-based metal alloy to result in the increased elastic modulus is performed from approximately 150° C. to approximately 400° C. for approximately 30 minutes to approximately 168 hours.

9. The method of claim 7, wherein the heat treating at least one first portion of the Ti-based metal alloy to result in the increased elastic modulus comprises a stress induced phase transformation from the beta-phase crystalline structure to an omega-phase crystalline structure.

10. The method of claim 1, further comprising heat treating the Ti-based metal alloy to strengthen the Ti-based metal alloy before the heat treating at least one first portion of the Ti-based metal alloy to result in the decreased elastic modulus.

11. The method of claim 10, wherein the heat treating the Ti-based metal alloy to strengthen the Ti-based metal alloy comprises creating an inconsistent omega-phase crystalline structure.

12. The method of claim 11, wherein the heat treating the Ti-based metal alloy to strengthen the Ti-based metal alloy is performed at a temperature from approximately 150° C. to approximately 400° C.

13. The method of claim 4, further comprising tuning heat treating the Ti-based metal alloy after the heat treating at least one first portion of the Ti-based metal alloy to result in the decreased elastic modulus, wherein the tuning heat treating is performed at a temperature of from approximately 150° C. to approximately 400° C. for approximately 30 minutes to approximately 168 hours, wherein the tuning heat treating the Ti-based metal alloy comprises creating an omega-phase crystalline structure.

14. A method of making a variably elastic metal alloy product comprising:
    casting a Ti-based metal alloy to obtain a cast Ti-based metal alloy comprising a beta-phase crystalline structure and an intermediate elastic modulus;
    cold working the cast Ti-based metal alloy;
    after the cold working, heat treating at least one first portion of the Ti-based metal alloy to train the at least one first portion of the Ti-based metal alloy to result in a decreased elastic modulus that is lower than the intermediate elastic modulus or to result in an increased elastic modulus that is higher than the intermediate elastic modulus; and during the heat treating at least one first portion of the Ti-based metal alloy, maintaining the intermediate elastic modulus of at least one second portion not subjected to heat treating, wherein the heat treating at least one first portion of the Ti-based metal alloy and the maintaining the intermediate elastic modulus of at least one second portion provides the variably elastic metal alloy product.

15. The method of claim 14, wherein the beta-phase crystalline structure comprises at least about 70% of the cast Ti-based metal alloy, and wherein the heat treating at least one first portion of the Ti-based metal alloy to result in the decreased elastic modulus is performed at a temperature from approximately 150° C. to approximately 1200° C. for approximately 1 minute to approximately 20 minutes.

16. A method of making a variably elastic metal alloy product comprising:

casting a metal alloy comprising a beta-phase crystalline structure, wherein the metal alloy comprises 70 atomic percent (at. %) to 78 at. % Ti, 18 at. % to 24 At. % Nb, up to 12 at. % of a third alloying element selected from the group consisting of zirconium (Zr), tin (Sn), chromium (Cr), molybdenum (Mo), iron (Fe), and tantalum (Ta), and up to 1 at. % of impurities;

heat treating at least one first portion of the metal alloy to train the at least one first portion of the metal alloy to result in a decreased elastic modulus that is lower than an elastic modulus of at least one second portion of the variably elastic metal alloy product not subjected to heat treating or to result in an increased elastic modulus that is higher than the elastic modulus of the at least one second portion of the variably elastic metal alloy product not subjected to heat treating; and during the heat treating at least one first portion of the metal alloy, maintaining the elastic modulus of the at least one second portion of the metal alloy not subjected to heat treating to provide the variably elastic metal alloy product, wherein the variably elastic metal alloy product comprises at least one rigid portion and at least one flexible portion.

17. The method of claim 16, wherein the heat treating at least one first portion of the metal alloy and the maintaining the elastic modulus of the at least one second portion of the metal alloy not subjected to heat treating further comprises providing a plurality of rigid portions having an elastic modulus of from approximately 80 GPa to approximately 110 GPa, and a plurality of flexible portions having an elastic modulus of from approximately 20 GPa to approximately 40 GPa.

18. The method of claim 17, further comprising controllably distributing the plurality of rigid portions and the plurality of flexible portions across the variably elastic metal alloy product.

19. The method of claim 16, wherein the maintaining the elastic modulus of the at least one second portion not subjected to heat treating comprises thermally insulating, direct contact chilling, air cooling, or gas flow cooling the at least one second portion.

20. The method of claim 16, further comprising cold working the metal alloy after the casting and before the heat treating at least one first portion of the metal alloy.

21. The method of claim 20, wherein the heat treating at least one first portion of the metal alloy to result in the decreased elastic modulus is performed at a temperature from approximately 150° C. to approximately 1200° C. for approximately 1 minute to approximately 20 minutes.

22. The method of claim 16, wherein the beta-phase crystalline structure comprises at least about 70% of the cast metal alloy.

* * * * *